United States Patent [19]

Csonka et al.

[11] Patent Number: 4,594,323
[45] Date of Patent: Jun. 10, 1986

[54] HYBRID DNA CONFERRING OSMOTIC TOLERANCE

[75] Inventors: Laszlo N. Csonka; Raymond C. Valentine, both of Davis, Calif.

[73] Assignee: The Regents of the University of California, Berkeley, Calif.

[21] Appl. No.: 570,410

[22] Filed: Jan. 12, 1984

Related U.S. Application Data

[63] Continuation of Ser. No. 421,666, Sep. 22, 1982, abandoned, which is a continuation-in-part of Ser. No. 259,318, Apr. 30, 1981, abandoned.

[51] Int. Cl.⁴ .................. C12P 13/24; C12N 15/00; C12N 1/20; C07H 19/10
[52] U.S. Cl. .................. 435/107; 435/172.3; 435/253; 435/317; 935/14; 935/29; 935/60; 536/27
[58] Field of Search ............ 435/107, 110, 172, 68, 435/317, 253, 172.3; 935/29, 60, 14; 536/27

[56] References Cited

U.S. PATENT DOCUMENTS 4,237,224 12/1980 Cohen et al. .................. 435/172
4,278,765 7/1981 Debabove et al. .................. 435/172

FOREIGN PATENT DOCUMENTS 2075056 10/1981 United Kingdom .................. 435/172
2076853 12/1981 United Kingdom .................. 435/172

Primary Examiner—Esther M. Kepplinger
Assistant Examiner—Patricia L. De Santis
Attorney, Agent, or Firm—Bertram I. Rowland

[57] ABSTRACT

Non-conjugative episomes characterized by having a mutated proBA region are provided for conferring osmotic tolerance on osmotically sensitive hosts. The mutated DNA sequence overproduces at least one enzyme in the biosynthetic pathway for an amino acid which imparts the desired osmotic tolerance.

Cell lines *E. coli* CSH26 were deposited at the A.T.C.C. on Sept. 20, 1982 and given accession number 39202.

14 Claims, 2 Drawing Figures

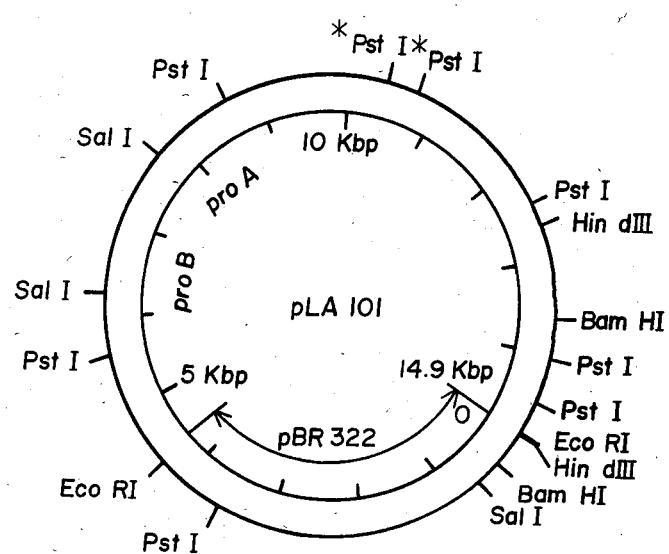
FIG._1
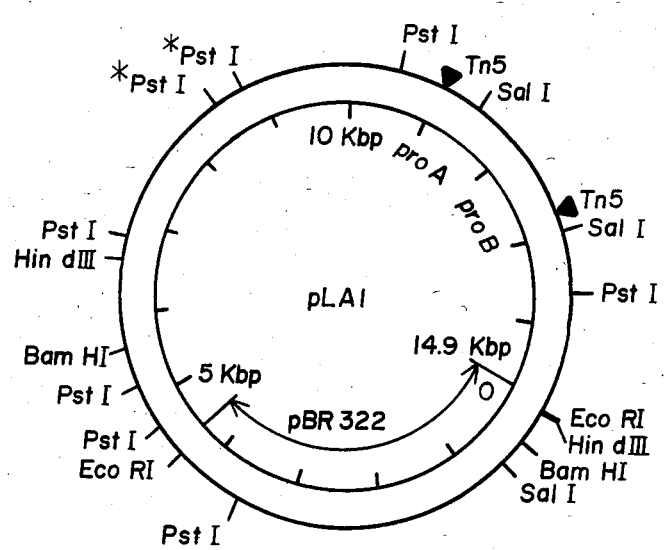
FIG._2

HYBRID DNA CONFERRING OSMOTIC TOLERANCE

The Government has rights in this invention pursuant to the Grant No. PFR 77-07301 ordered by the National Science Foundation.

CROSS-REFERENCE TO RELATED APPLICATIONS

This is a continuation of Ser. No. 421,666, filed Sept. 22, 1982, abandoned, which is a continuation-in-part of Ser. No. 259,318, filed Apr. 30, 1981, abandoned.

BACKGROUND OF THE INVENTION

1. Field of the Invention

In many situations, it is desirable that cells, such as microorganisms, plant cells, mammalian tissues, or the like be able to withstand elevated osmotic pressures. For a variety of reasons it may be desirable or necessary for cells to grow in or tolerate an environment having enhanced osmolarity. For example, where hybrid DNA technology is involved, it could be desirable to use a relatively concentrated nutrient medium, where the constituents of the nutrient medium result in an elevated osmotic pressure. With plants, it will be desirable to be able to employ low grade waters having elevated saline content. Alternatively, many soils due to continued irrigation or other reasons have increased their salinity. In both situations, the ability for plant cells to grow in an environment having enhanced salinity would be very useful in increasing the amount of arable land.

It would therefore be desirable to provide ways to permit cells to grow in or tolerate an environment of enhanced osmolarity. By having such cells, one could greatly expand the conditions under which cells can be grown.

2. Description of the Prior Art

Csonka, Genetic Engineering of Osmoregulation (1980) eds. Rains, Valentine and Hollaender, Plenum Publising Corp., New York, describes the role of L-proline in response to osmotic stress. That article and the references contained therein, particularly the references referred to on pages 35–36 should be noted. Condamine, Annales de Institut Pasteur, Paris 120, 126–142 (1972) indicates that proline over-production may be a result of alteration of the first enzyme of the proline biosynthetic pathway. Csonka (1981) Mol. Gen. Genet. 182:82–86 describes the isolation of Salmonella typhimurium TL126 including mutant proBA genes on an F'-plasmid which provide for the overproduction of proline and confer osmotic tolerance.

SUMMARY OF THE INVENTION

Methods and compositions are provided for conferring osmotic tolerance on an osmotically sensitive host. An extrachromosomal element includes a non-conjugative vector and a DNA sequence capable of expressing an enzyme in the biosynthetic pathway from 2-ketoglutarate to L-proline. The DNA sequences are inducible in hypertonic growth media leading to the overproduction of the amino acid(s), which in turn enhances the osmotic tolerance of the host. The vectors may be introduced into the osmotically sensitive host by conventional techniques to confer the desired osmotic tolerance.

DESCRIPTION OF THE SPECIFIC EMBODIMENTS

Cells are genetically manipulated to display enhanced osmotic tolerance by virtue of overproduction of amino acids imparting protection against elevated osmolarity in the environment in which the cells are grown. Particularly, the cells are modified by introducing at least one gene encoding an enzyme in the biosynthetic pathway of an amino acid as a part of an exogenous extrachromosomal DNA sequence capable of replication and expression in the host. One or more genes of the metabolic biosynthetic pathway for the amino acids L-proline, L-glutamine or L-glutamate, particularly a gene expressing an enzyme at an early and/or rate limiting stage of the biosynthetic pathway, preferably a first stage from a substrate which is an amino acid or 2-ketoglutarate, may be introduced into a cell under conditions allowing for selection of cells having the gene(s) which allow for over-production of one or more of the above indicated amino acids.

The genes of interest include those involved in the biosynthetic pathway to L-proline beginning with 2-ketoglutarate. These genes express the following enzymes: glutamic dehydrogenase which catalyzes the pyridine nucleotide-linked formation of glutamic acid from 2-ketoglutarate and ammonia; glutamine synthetase, which catalyzes the ATP linked formation of glutamine from glutamic acid and ammonia; a pyridine nucleotide linked glutamate synthase which catalyzes the pyridine nucleotide linked formation of glutamate from glutamine and 2-ketoglutarate; glutamate kinase, which catalyzes the formation of γ-glutamyl phosphate from glutamate and ATP; glutamic-γ-semialdehyde dehydrogenase, which catalyzes the pyridine nucleotide linked formation of glutamic-γ-semialdehyde from γ-glutamyl phosphate; and an enzyme which catalyses the reduced pyridine nucleotide reductive formation of proline from glutamic-γ-semialdehyde.

The compositions which find use in this invention for introduction of the gene(s) will be extrachromosomal elements, having replication systems from plasmids and viruses (including phage), which have been genetically manipulated in vitro, and the clones, progeny and derivatives of such extrachromosomal elements. Various plasmids may be employed, derived from R-plasmids, Ti-plasmids, colicin plasmids, pRK290-2031 system (Ditta et al, PNAS USA, 77:7347 (1980), 2μ-plasmid, etc. The plasmids are non-conjugative being introduced into the host by transformation. The particular choice of the plasmid will depend upon the host, the availability of plasmids having the desired restriction sites, markers, and regulatory signals, the efficiency of introduction of the plasmid, the stability of the plasmid, the copy number, and the like. The significant factors concerning the plasmids will be that they have a replication system recognized by the host, have available restriction sites for introduction of the desired gene(s) and regulatory DNA sequences, desirably, a marker will be present which will allow for selection of the cells having the plasmids, the plasmid will be stable and in some situations, capable of having a controlled copy number under predetermined conditions.

The viruses (including phages) will also depend upon the host, the ability to introduce the gene(s) and other regulatory signals into the virus, whether the virus can be stably integrated into the chromosome, whether avirulent strains are available, and similar considerations referred to in relation to plasmids. Various viruses of interest include lambda, M13 cauliflower mosaic virus, fd, T-even and T-odd phage, P1, P22, etc.

References describing various techniques for stably introducing exogenous vectors into a variety of cells include: Genetic Engineering, Vol 1, eds. Setlow and Hollaender, Plenum Press, New York and London, 1979; Kornberg, DNA Replication, W. H. Freeman and Co., San Francisco, 1980; Curtiss, Ann. Rev. of Microbiology 23:69-136 (1969); Molecular Cloning of Recombinant DNA eds. Scott and Werner, Academic Press, New York, 1977; and Old and Primrose, Principles of Gene Manipulation, U. of California Press (1981).

Osmotic tolerance intends osmolarity above the isotonic osmolarity at the basal level of production of the amino acids. Hypertonic solutions are those having a higher osmolarity than the cytoplasm.

Since the subject invention is concerned with providing osmotic tolerance, the host cells may vary widely. For the most part, the cells will not be mammalian cells, but may be cells of other vertebrates. Usually the host will be a single celled organism, such as bacteria, protozoa, algae, fungi e.g. yeast, or plants, such as rhodophycophyta, phaeophycophyta and euchlorophyta, particularly pinopsida, dictyledonae and monocotyledonae. The host cells will normally have a basal level of production of the desired amino acid(s), usually subject to an intact regulatory system(s). The host cell will be a cell which is to be grown under conditions where the osmotic tolerance will provide a selective advantage for the cell. In growing microorganisms, cells and tissues, there may be situations where the nutrient medium will have or will result in elevated osmolarity. The ability to be able to grow microorganisms efficiently at high osmotic pressures will provide substantial advantages in allowing for enhanced concentration of solutes in the nutrient medium. Therefore, in those situations where over-production of an amino acid imparting osmotolerance does not interfere with the desired production of the expression products of heterologous genes, the capability of overproducing an amino acid providing osmotolerance can be of decided advantage.

Of particular interest is the modification of plant cells, where the plants can accept water having elevated osmolarity, particularly salinity, such as brackish water, sea water, irrigation water, and the like.

Other situations where osmotolerance may be desirable is the use of organisms for removal of pollutants from sea water, growing plants in saline soil, removal of oil spills on the seas and beaches, and the like.

The cells which are modified by the introduction of the genes will desirably have a basal level of production of the amino acid to be overproduced. For the most part, the enzyme catalyzed reactions in the early stages of the biosynthetic pathway involve one or more rate limiting step(s), so that it is usually sufficient to provide one or more of the genes expressing the enzymes of the early or rate limiting steps to provide for the enhanced production of the desired amino acid. By early stage is intended a stage starting with a nutrient generally available to the host for preparing the amino acid.

Besides overproduction of enzyme to provide for the overproduction of an amino acid, a gene(s) expressing an isozyme(s) which overproduces the desired intermediate in the biosynthetic pathway can also be employed. The overproduction may be as a result of enhanced activity, inefficient feed-back inhibition, or the like.

The hybrid DNA technology requires isolation of the gene(s) which are to be introduced into the host from a source of the gene, usually the DNA from a microorganism which has been acclimated to a hypertonic growth medium. By appropriate restriction mapping, one can isolate the intact gene having greater or lesser sequences extending from the gene. Whether the gene includes regulatory signals from its source will depend to some degree on the available restriction sites, the capability of the host to recognize the foreign regulatory signals and upon the intended host. The DNA fragment containing the gene may be processed by removal of nucleotides using endo- or exonucleases, addition of linkers, blunt end formation employing DNA polymerase, chain extension employing individual nucleotides or oligonucleotides, or the like. The DNA sequence of interest is then incorporated into a vector which has a replicating system recognized by the desired host. The replicating system will be derived from a plasmid or a virus. In addition to the replicating system, other regulatory signals may be present as part of the vector or may be introduced. Included among the regulatory signals are promoters, operators, initiators, terminators, ribosomal start and stop sites, CAP sites, or the like. The various sequences may be joined in accordance with conventional ways, by annealing where cohesive ends are available, and ligation. By appropriate strategies, vectors can be chosen having restriction sites to permit introduction of the gene(s) of interest as well as the regulatory signals as required.

It will usually be desirable to provide the vector with a marker to allow selection of transformants. Markers of particular interest are those which provide protection from biocidal reagents or provide prototrophy to an auxotrophic host. The choice of marker will vary with the nature of the host. With microorganisms, genes expressing enzymes providing antibiotic resistance, colicin resistance or resistance to a heavy metal are particularly useful. Genes providing resistance to viruses can also serve as markers. Plants markers may include folic acid antagonists e.g. methotrexate.

As illustrative of the present invention, the DNA sequence may be derived from a mutant which overproduces an amino acid as set forth above. One method for detection of such mutants is to employ an analog of the particular amino acid which is lethal when employed as a metabolite or incorporated into a polypeptide. Overproduction of the particular amino acid will dilute the toxic analog, allowing the mutant strain to survive under conditions which are lethal to the wild-type microorganism.

Illustrative of the use of such analogs is the use of L-azetidine-2-carboxylate as an analog of L-proline. A particular mutant of Salmonella typhimurium, namely TL126 (A.T.C.C. accession no. 31875) includes a mutation of the proBA region on the endogenous F'-plasmid resulting in the overproduction of L-proline.

The mutated proBA region can be excised from the F'-plasmid by conventional techniques. In particular, digestion with Eco RI yields a 14.9 kbp DNA fragment including the proBA region. A shorter fragment on the order of 4.9 kbp may be obtained by partial digestion of the Eco RI fragment with Pst I.

The following examples are offered by way of illustration and not by way of limitation.

EXPERIMENTAL

Materials and Methods

Bacterial Strains and Plasmids

The bacterial strains and plasmids used in these experiments are listed in Table 1.

Culture Media

The minimal media used was M63, pH 7.2 (Cohen and Rickenberg (1956) Ann. Inst. Pasteur, Paris 91:693-720). D-glucose (20 g/liter) was the carbon source. When required, L-amino acids were added at a concentration of 25 μ/ml. The rich media use Luria Broth. Solid media contained an additional 20 g/liter of agar (Difco). When required, final concentrations of ampicillin (30 μg/ml), tetracycline (20 μg/ml), kanamycin (200 μg/ml), streptomycin (1 mg/ml), L-azetidine-2-carboxylate (0.5 mM), were added.

Restriction Endonucleases and Enzymes

Isolation of Plasmid DNA

Plasmid DNA was obtained from overnight cultures grown in Luria Broth. All plasmid DNA was isolated by the alkaline lysis technique of Hasen and Olsen (1978) J. Bacterial 135:227-238.

Agarose Gel Electrophoresis

Electrophoresis of DNA was performed in 0.9% agarose gels (unless otherwise stated) in 89 mM tris base, 89 mM borate, 2.8 mM Na2EDTA, using a horizontal slab gel apparatus at 15 mA for 15 hrs at room temperature.

P22 Transduction

P22 transduction was performed by the technique of Davis, Botstein, and Roth (1980). *Advanced Bacterial Genetics*, Cold Springs Harbor, pp. 84-88.

TABLE 1

| Strain | Chromosome Genotype | Plasmid | Source or Method of Derivation |
|---|---|---|---|
| *E. coli* K-12 | | | |
| RRI | proBA, leu, B1, hsdRM | none | R. C. Tait |
| CSH26 | proBA | none | T. Messing |
| PCO450 | Hfr, artIF, thr, leu, proA, relA, tonA | none | B. Bochman |
| CM25 | same as RRI | pLA1 | RRI transformed to proB$^+$A$^+$ by pLA1 |
| CM26 | same as CSH26 | pLA1 | CSH26 transformed to proB$^+$A$^+$ by pLA1 |
| CM27 | same as CSH26 | pLA2 | CSH26 transformed to proB$^+$A$^+$ by pLA2 |
| CM28 | same as CSH26 | pLA3 | CSH26 transformed to proB$^+$A$^+$ by pLA3 |
| CM125 | same as RRI | pLA101 | RRI transformed to proB$^+$A$^+$ by pLA101 |
| CM126 | same as CSH26 | pLA101 | CSH26 transformed to proB$^+$A$^+$ by pLA101 |
| CM128 | same as CSH26 | pLA103 | CSH26 transformed to proB$^+$A$^+$ by pLA103 |
| *S. typhimurium* LT-2 | | | |
| JL2468 | del(proBA)47, leuD798, arg 1537, ara9, fol-1 | F'$_{128}$ proB$^+$A$^+$ argF$^+$ lacI$^q$::Z$^+$Y$^+$A$^+$ | J. Ingraham |
| TL88 | same as JL2468 | F' pro-74(L-azetidine-2-carboxylate derivative of F'$_{128}$ in JL2468) | MGG 1981 |
| TL117 | del(proBA)47 | none | MGG 1981 |
| TL128 | same as TL117 | F'$_{128}$ | MGG 1981 |
| TL126 | same as TL117 | F'pro-74 | MGG 1981 (ATCC Acc. No. 31875) |
| SL4213 | same as SL4213 | pLA1 | SL4213 transformed to Tc$^r$ by pLA1 |
| TL245 | same as SL4213 | pLA2 | SL4213 transformed to Tc$^r$ by pLA2 |
| TL246 | same as SL4213 | pLA3 | SL4213 transformed to Tc$^r$ by pLA3 |
| TL247 | same as SL4213 | pLA101 | SL4213 transformed to Tc$^r$ by pLA101 |
| TL248 | same as SL4213 | pLA103 | SL4213 transformed to Tc$^r$ by pLA103 |
| TL249 | same as TL117 | pLA101 | TL117 transformed to proB$^+$A$^+$ by pLA101 |
| TL250 | same as TL117 | pLA1 | TL117 transformed to proB$^+$A$^+$ by pLA1 |
| PROA39 | proA | none | K. Sanderson |
| PROB9 | proB | none | K. Sanderson |
| TL159 | del(proBA)47::TN5 | F'$_{128}$ | L. N. Csonka |
| TL158 | same as TL159 | F'pro-74 | L. N. Csonka |
| JL2202 | del(proBA)47, pyrA, str$^r$ | none | J. Ingraham |
| TL255 | same as JL2202 | F'$_{128}$ proA1655::Tn5 | Km$^r$, Str$^r$ progeny of mating JL2202 × TL159 |
| TL243 | same as J12202 | F'$_{128}$ proB1558::Tn5 | KM$^r$, Str$^r$ progeny of mating JL2202 × TL159 |
| TL246 | same as JL2202 | F' pro-74 proA1660::Tn5 | Km$^r$, Str$^r$ progeny of mating JL2202 × TL158 |
| TL251 | same as PROB9 | pLA4 | Km$^r$, proA::Tn5 derivative of pLA1 |
| TL252 | same as PROA39 | pLA4 | Km$^r$, proA::Tn5 derivative of pLA1 |
| TL253 | same as PROB9 | pLA5 | Km$^r$, proB::Tn5 derivative of pLA1 |
| TL254 | same as PROA39 | pLA5 | Km$^r$, proB::Tn5 derivative of pLA1 |

Eco RI, Sal I and T4 DNA ligase were obtained from R. C. Tait. Hin dIII, Bam HI, and Pst I were obtained from New England Biolabs.

Results

Cloning of the Osmotolerant Mutation Region

Total DNA from an osmotically tolerant, proline overproducing mutant, TL88 (F' pro-74), and its wild type parent, JL2468 (del(proBA)47 /F'$_{128}$ proB+A+), was isolated and digested with Eco RI. The resultant fragments were inserted into the Eco RI site of pBR322. The hybrid DNA was transformed into E. coli strain RRI (hsdRM, del(proBA)), and proline prototrophic transformants (Pro+) were selected. The Pro+ transformants were then scored for resistance to L-azetidine-2-carboxylate (Azt$^r$), a toxic analog of proline. Overproduction of proline will dilute the toxic analog, and resistance to the analog is an effective screen for clones with the proline overproducing phenotype. All (16/16) proline prototrophic progeny that were transformed with DNA from TL88 were Azt$^r$, while all prototrophic progeny that were transformed with DNA from JL2468 were Azt$^s$.

Plasmid DNA was isolated from one of the osmotically tolerant progeny, CM125 (RRI transformed with TL88 DNA), and from one of the osmotically sensitive progeny, CM25 (RRI transformed with JL2468 DNA). The plasmid DNA was transformed into E. coli strain CSH26 (del(proBA)). Again, proline prototrophic clones were selected for on minimal medium and scored for Azt$^r$. All CM125 plasmid (designated as pLA101) transformants, such as CM126, had the proline overproducing phenotype, and all CM25 plasmid (designated as pLA1) transformants, such as CM26, did not have the proline over-producing phenotype.

Properties of the Recombinant Plasmids

Restriction maps of the recombinant plasmids were prepared and are set forth in FIG. 1 (pLA101) and FIG. 2 (pLA1). The orientation of the starred (*) Pst I sites were not determined. Although the recombinant plasmids were cloned in opposite orientations with respect to pBR322, both pLA1 and P1A101 contain 14.9×10$^3$ base pairs (14.9 kb) of DNA, which contain the proBA biosynthetic genes on a 10.6 kb Eco RI fragment.

In order to obtain small plasmids containing the proBA biosynthetic genes, fragments of pLA101 and pLA1 were subcloned. Both pLA1 and pLA101 were partially digested with Pst I, followed by religation and transformation into CSH26(del proBA), selecting proline prototrophy (Pro+). The resultant transformants were screened for lower molecular weight plasmids. The lowest molecular weight plasmid obtained which carried the proBA biosynthetic genes was named pLA2, a subclone of pLA1. pLA2 was identified genetically as Amp$^s$, Tc$^r$, and Azt$^s$. The corresponding pLA101 sub-clone, pLA103, was identified genetically as Amp$^r$, Tc$^r$ and Azt$^r$. The recombinant plasmids were transformed into S. typhimurium for subsequent analysis. The host specificity determinant locae (hsdRM) in S. typhimurium code for a different restriction modification system than the hsdRM locae in E. coli. Therefore, in order to avoid a restriction problem, the plasmid DNA was first transformed into a restriction deficient, modification proficient, S. typhimurium strain SL4213, selecting for the presence of the plasmid by resistance to tetracycline and screening for resistance to ampicillin. The modified DNA was isolated and transformed into TL117 (del(proBA)47), selecting proline prototrophy. The resulting osmotolerant progeny was named TL249 (TL117 transformed with pLA101), while the osmotically sensitive progeny was named TL250 (TL117 transformed with pLA1).

Osmotolerance Phenotype

The following experiments confirm that the azetidine resistant phenotype is an effective screen for colonies that are osmotically tolerant. The stimulation of the growth rate of S. typhimurium strain TL117 (del(-proBA)47) by various recombinant plasmids in the presence of 0.65 M NaCl is exhibited in Table 2.

TABLE 2

| Plasmid | Growth Rate |
|---|---|
| F' (pro B+A+, Azt$^s$) | 0.19 gen./hr. |
| F' (pro-74, Azt$^r$) | 0.33 gen./hr. |
| pLA101 (pro-74) | 0.25 gen./hr. |
| pLA101 (opp. orientation) | 0.26 gen./hr. |

The growth stimulation achieved by insertion of the pro-74 mutation is approximately twice that of the wild-type proB+A+ for both the F' plasmid and the pBR322-derived plasmids. The following qualitative observations were also made. First, the presence of pLA101 or pLA1 significantly decreases the growth rate of TL117 when the culture is grown in minimal medium without salt. The presence of one or more genes on the recombinant plasmids appears to be deleterious to the cell. Second, pLA101 significantly increases the generation time of TL117 compared to pLA1 when the culture is grown in minimal medium without salt.

Transposon Insertion and Complementation

The genes that code for gamma glutamylkinase (proB) and for gamma glutamylphosphate dehydrogenase (proA) were identified genetically by transposition insertion and complementation experiments. The transposition of TN5 into the proBA biosynthetic genes was selected for by the ability to transfer kanamycin resistance (Km$^r$). The Km$^r$ progeny were then scored for the ability to ferment lactose (Lac+) and proline auxotrophy (Pro−). This was accomplished by mating the osmotically tolerant strain, TL158 (del(-proBA)47::Tn5 F' pro74) and the osmotically sensitive strain, TL159 (del(proBA)47::Tn5 F'$_{128}$) with JL2202 (del(proBA)47 pyrA, Str$^r$). Km$^r$, Str$^r$ progeny were selected on Luria Broth and scored for Pro−, which indicates the Tn5 inserted into one of the proBA biosynthetic genes. Next, the region of insertion was identified genetically by complementation experiments. The Km$^r$, Str$^r$, Lac+, Pro− colonies were mated with PROA39 (proA), and PROB9 (proB). Pyr A+, Km$^r$ progeny were selected for in minimal medium with the addition of proline. The resultant colonies were scored for Lac+ and Pro−.

TABLE 3

| Strain | Plasmid | Parental Strain | |
|---|---|---|---|
| | | PROA39 | PROB9 |
| TL128 | F'$_{128}$ | + | + |
| TL117 | none | − | − |
| TL243 | F'$_{128}$ proB1658::Tn5 | + | − |
| TL255 | F'$_{128}$ proA1655::Tn5 | − | + |
| TL256 | F' pro-74 proA1660::Tn5 | − | + |
| TL244 | pLA1 | + | + |
| TL251 | pLA4 | − | + |
| TL252 | pLA4 | − | + |
| TL253 | pLA5 | + | − |
| TL254 | pLA5 | + | − |

Referring to Table 3, TL255 and TL243 have a Tn5 insertion in proA, and TL256 has a Tn5 insertion in proB.

The next experiment was to transduce the Tn5 insertions into the proBA biosynthetic genes of the cloned plasmid, pLA1, so a physical location of proA and proB could be delineated by restriction endonuclease mapping. P22 lysates of TL255 (JL2202 with F' proA::Tn5) and TL256 (JL2202 with F' proB::Tn5) were used to transduce TL250 (TL117 transformed with pLA1) to kanamycin resistance. The Km$^r$ clones obtained were scored for proline prototrophy. As shown in Table 3, TL251 has a Tn5 insertion in the proA gene of pLA1, and TL254 has a Tn5 insertion in the proB gene of pLA1. Plasmid DNA from TL251, pLA4 (proA::Tn5), and from TL254, pLA5 (proB::Tn5), was isolated, and restriction endonuclease mapping depicted the physical location of the biosynthetic genes of proA and proB. The Tn5 insertions are illustrated as arrows on FIG. 2.

It is evident from the above results, that one can induce osmotolerance in a wide variety of host cells by introducing a vector including at least a portion of the proBA genes, which has been mutated to provide for overproduction of amino acids imparting osmotic tolerance, such as the amino acids proline, glutamine and glutamate. By employing any of the numerous techniques for introducing such vectors, elevated osmolarity of the medium can trigger enhanced production of the amino acids and osmotolerance of the cell. This technique can be applied to a wide variety of cells to provide for protection for the cells and enhanced growth in osmotically hostile environments.

Although the foregoing invention has been described in some detail be way of illustration and example for purposes of clarity of understanding, it will be obvious that certain changes and modifications may be practiced within the scope of the appended claims.

We claim:

1. An extrachromosomal element comprising a non-conjugative vector capable of stable replication and expression in a preselected host and a bacterial DNA sequence having the pro-BA genes ligated therein and coding for enzymes in the biosynthetic pathway from 2-ketoglutarate to L-proline which sequence is inducible in a hypertonic medium, said vector being capable of conferring osmotic tolerance on a compatible host, or clones thereof.

2. An extrachromosomal element according to claim 1, wherein the enzymes are γ-glutamylkinase and γ-glutamylphosphate dehydrogenase.

3. An extrachromosomal element as in claims 1 or 2, wherein said vector is derived from pBR322.

4. An extrachromosomal element as in claims 1 or 2, wherein said DNA sequence is inserted in the EcoRI site of pBR322.

5. pLA101.

6. A method for conferring osmotic tolerance on an osmotically-sensitive host, said method comprising:
transforming a compatible microorganism host with a non-conjugative extrachromosomal element capable of stable replication in said host and having a bacterial DNA sequence including the proBA gene expressing enzymes in the biosynthetic pathway from 2-ketoglutarate to L-proline and being inducible in a hypertonic medium, and;
growing said microorganism hose in a suitable growth medium.

7. A method as in claim 6, wherein the microorganism is a bacterium.

8. A method as in claim 6, wherein the DNA sequence includes genes expressing both γ-glutamyl phosphate dehydrogenase and γ-glutamylkinase.

9. A method as in claim 6, wherein the extrachromosomal element is pLA101.

10. An osmotically-tolerant bacterium produced according to the method of claims 7 or 9.

11. A DNA fragment carrying an approximately 4.9 kbp region including the proBA genes, said fragment being free from other genes in the biosynthetic pathway from 2-ketoglutarate to L-proline.

12. An extrachromosomal element comprising a non-conjugative vector capable of stable replication in a preselected host and a DNA sequence joined to the vector, said DNA sequence capable of expressing at least two enzymes in the biosynthetic pathway from 2-ketoglutarate to L-proline and conferring osmotic tolerance on a compatible host.

13. An extrachromosomal element as in claim 12, wherein the enzymes are γ-glutamylkinase and γ-glutamylphosphate dehydrogenase.

14. An extrachromosomal element as in claim 12, wherein the DNA sequence is inserted into the EcoRI site of pBR322.

* * * * *

UNITED STATES PATENT AND TRADEMARK OFFICE
CERTIFICATE OF CORRECTION

PATENT NO. : 4,594,323

DATED : June 10, 1986

INVENTOR(S) : Csonka et al.

It is certified that error appears in the above-identified patent and that said Letters Patent is hereby corrected as shown below:

ON THE TITLE PAGE, ITEM [75], should read

-- [75] Laszlo N. Csonka; Raymond C. Valentine; Michael J. Mahan, all of Davis, Calif. --.

Signed and Sealed this

Twenty-second Day of December, 1987

Attest:

DONALD J. QUIGG

*Attesting Officer*  *Commissioner of Patents and Trademarks*